US009355219B2

(12) United States Patent
Paydar et al.

(10) Patent No.: US 9,355,219 B2
(45) Date of Patent: May 31, 2016

(54) DISPENSING CABINET WITH ARTICULATING ARM

(75) Inventors: Akbar Paydar, Mountain View, CA (US); Stanley Kim, Mountain View, CA (US); Chris Richardson, Mountain View, CA (US); John Foot, Mountain View, CA (US); Mahmoud Amini, Mountain View, CA (US); Stuart Morita, Mountain View, CA (US)

(73) Assignee: Omnicell, Inc., Mountain View, CA (US)

( * ) Notice: Subject to any disclaimer, the term of this patent is extended or adjusted under 35 U.S.C. 154(b) by 222 days.

(21) Appl. No.: 13/461,392

(22) Filed: May 1, 2012

(65) Prior Publication Data

US 2012/0323362 A1 Dec. 20, 2012

Related U.S. Application Data

(60) Provisional application No. 61/481,577, filed on May 2, 2011.

(51) Int. Cl.
*G07F 17/00* (2006.01)
*G06F 19/00* (2011.01)
*G07F 11/00* (2006.01)
*G07F 11/62* (2006.01)
*A61G 12/00* (2006.01)

(52) U.S. Cl.
CPC .......... *G06F 19/3462* (2013.01); *A61G 12/001* (2013.01); *G07F 11/002* (2013.01); *G07F 11/62* (2013.01); *G07F 17/0092* (2013.01); *Y10T 29/4984* (2015.01)

(58) Field of Classification Search
CPC ... G07F 17/0092; A61J 7/0069; A61J 7/0076; A61J 7/0084; A61G 12/001; G06F 19/3462; A61B 19/0248
See application file for complete search history.

(56) References Cited

U.S. PATENT DOCUMENTS 4,695,024 A * 9/1987 Haven ...................... 248/281.11
4,836,486 A * 6/1989 Vossoughi et al. ........ 248/281.11
(Continued)

FOREIGN PATENT DOCUMENTS

WO 99/04686 A1 2/1992

OTHER PUBLICATIONS

International Search Report and Written Opinion of PCT/US2012/035148 mailed on Jul. 11, 2012, 9 pages.
(Continued)

*Primary Examiner* — Timothy Waggoner
(74) *Attorney, Agent, or Firm* — Kilpatrick Townsend & Stockton LLP

(57) ABSTRACT

It may be advantageous to equip a medication dispensing cart with an adjustable user interface. An exemplary dispensing device may include a cabinet having one or more compartments for dispensing health care supplies to one or more patients. The dispensing device may also include a control system that provides various operational functions related to dispensing the health care supplies. A user interface may be communicatively coupled with the control system and may be configured to receive input from a user and provide output to the user. An articulating arm assembly may couple the user interface with the cabinet to provide the user interface with one or more translational degrees of freedom and one or more rotational degrees of freedom relative to the cabinet.

13 Claims, 11 Drawing Sheets

(56) References Cited

U.S. PATENT DOCUMENTS

| | | | |
|---|---|---|---|
| 5,190,185 A | 3/1993 | Blechl | |
| 5,377,864 A | 1/1995 | Blechl et al. | |
| 5,745,366 A | 4/1998 | Higham et al. | |
| 5,805,455 A | 9/1998 | Lipps | |
| 5,805,456 A | 9/1998 | Higham et al. | |
| 5,905,653 A | 5/1999 | Higham et al. | |
| 5,927,540 A | 7/1999 | Godlewski | |
| 6,011,999 A | 1/2000 | Holmes | |
| 6,039,467 A | 3/2000 | Holmes | |
| 6,151,536 A | 11/2000 | Arnold et al. | |
| 6,170,929 B1 | 1/2001 | Wilson et al. | |
| 6,272,394 B1 | 8/2001 | Lipps | |
| 6,339,732 B1 * | 1/2002 | Phoon et al. | 700/237 |
| 6,385,505 B1 | 5/2002 | Lipps | |
| 6,604,019 B2 * | 8/2003 | Ahlin et al. | 700/231 |
| 6,609,047 B1 | 8/2003 | Lipps | |
| 6,640,159 B2 | 10/2003 | Holmes et al. | |
| 6,760,643 B2 | 7/2004 | Lipps | |
| 6,975,922 B2 | 12/2005 | Duncan et al. | |
| 6,980,419 B2 * | 12/2005 | Smith et al. | 361/679.41 |
| 7,210,598 B2 * | 5/2007 | Gerold et | 221/123 |
| 7,348,884 B2 | 3/2008 | Higham | |
| 7,461,825 B2 * | 12/2008 | Olivera et al. | 248/282.1 |
| 7,487,944 B2 * | 2/2009 | Tisbo et al. | 248/288.51 |
| 7,571,024 B2 | 8/2009 | Duncan et al. | |
| 7,675,421 B2 | 3/2010 | Higham | |
| 7,719,420 B2 * | 5/2010 | Christie et al. | 700/231 |
| 7,835,819 B2 | 11/2010 | Duncan et al. | |
| 8,286,977 B2 * | 10/2012 | Butler et al. | 280/47.35 |
| 8,469,323 B1 * | 6/2013 | Deros et al. | 248/278.1 |
| 8,593,278 B2 * | 11/2013 | Churbock et al. | 700/242 |
| 2003/0222548 A1 * | 12/2003 | Richardson et al. | 312/209 |
| 2008/0319579 A1 | 12/2008 | Vahlberg et al. | |
| 2009/0210089 A1 | 8/2009 | Christie et al. | |
| 2010/0042437 A1 | 2/2010 | Levey et al. | |

OTHER PUBLICATIONS

Extenden European Search Report in EP application No. 12779577.1, mailed on Oct. 22, 2014, 16 pages.

* cited by examiner

DISPENSING CABINET WITH ARTICULATING ARM

CROSS-REFERENCES TO RELATED APPLICATIONS

This application claims priority to Provisional U.S. Patent Application Ser. No. 61/481,577 filed May 2, 2011, entitled "Dispensing Cabinet With Articulating Arm," the entire disclosure of which is hereby incorporated by reference, for all purposes, as if fully set forth herein.

BACKGROUND OF THE INVENTION

The invention relates generally to medical cabinets and more specifically to medical cabinets having an adjustable user interface or computer terminal.

In a hospital or other patient care setting, a large number of medications and other medical supplies may be used to provide treatment to one or more patients. These medical supplies and/or medications are often stored in various dispensing devices, such as cabinets, drawers, compartments, and the like. These devices may also include other peripheral components that are used in the treatment of patients and/or for other purposes. Because dispensing devices may store various supplies and/or peripheral components that are used to treat a variety of patients, it is important that such dispensing devices minimize size while maximizing storage capacity and/or usage.

The dispensing devices may also include or otherwise be communicatively coupled with a computer that is designed to authorize users, track inventory, and/or perform other functions. The computer is often integrated within the dispensing device or rigidly attached thereto, such as by being attached to a top surface of the device. This configuration allows the computer to be transported with the dispensing device (in the case of a mobile device), but does not allow the computer to be adjusted relative to the device or minimizes any such adjustability.

Users working with the dispensing device may need to perform various different and sometimes unrelated tasks such as, for example, administering treatment to a patient, filling out paperwork, measuring and/or recording patient vital signs, scanning various documents, and the like. These different tasks often require that the dispensing device be used in different ways. For example, extra work space may be needed to fill out paperwork while quick access to the computer may be needed to access medical supplies and/or record vital signs. Because of the different tasks a user may be required to perform and/or the different usage requirement of the dispensing device, a need exists for a dispensing device that may be adjusted according to need and/or usage while minimizing device size and/or interference with other components.

BRIEF SUMMARY OF THE INVENTION

Embodiments of the invention provide methods, systems, and apparatus related to dispensing devices having an adjustable user interface. According to one embodiment, a dispensing device is provided. The dispensing device includes a cabinet having at least one compartment for dispensing health care supplies to one or more patients. The dispensing device also includes a control system having a processor and memory device. The control system may provide one or more operational functions related to dispensing the health care supplies, such as authenticating a user, unlocking the cabinet's compartment or a drawer or storage facility of the compartment, tracking and identifying supplies and/or medications, recording patient vital signs or other data, and the like.

A user interface may be communicatively coupled with the control system. The user interface may be configured to receive input from a user and provide output to the user such as, for example, to perform one or more of the operational functions described herein. An articulating arm assembly may be coupled with the user interface and the cabinet to provide the user interface with at least one and preferably three degrees of translational freedom and one degree of rotational freedom relative to the cabinet. To provide such movement, the articulating arm assembly may include a first arm that is rotationally coupled at a proximal end with the cabinet and may include a second arm that is rotationally coupled at a proximal end with a distal end of the first arm and that is rotationally coupled at a distal end with the user interface.

According to one embodiment, the first arm may be coupled with a side of the cabinet so that the articulating arm assembly provides the user interface with a barrel shaped range of motion relative to the cabinet. The barrel shaped range of motion may be interrupted on one side by the cabinet and may have a maximum barrel diameter of about 60 inches. The user interface is generally movable within the barrel shaped range of motion.

In one embodiment, the second arm may include a first joint that is disposed near the proximal end that allows the second arm to be vertically moved or adjusted relative to the first arm. The second arm may further include a second joint that is disposed near the distal end that allows the user interface to be rotationally adjusted relative to the second arm. The dispensing device may also include a third arm that couples the user interface with the second arm at the second joint. The third arm may extend laterally from the second joint. In one embodiment, the first arm may be coupled with a side of the cabinet near a top surface of the cabinet and near a back surface of the cabinet. This configuration may minimize the overall size of the device while providing a wide range of motion.

The user interface comprises a display device and a keyboard, the keyboard being rotationally adjustable relative to the display device. The control system may be configured to authenticate a user and to unlock a drawer, identify medication or supplies for a patient, track usage of a medication or supply, communicate information with a system of a health care facility, and the like. The cabinet may include one or more peripheral components such as: a fingerprint scanner, a card reader, a bar code scanner, a keyboard, a mouse, a display device, a printer, a camera, speakers, proximity sensor, a keypad or touchpad, and the like. One or more of the peripheral components may be coupled with the user interface and/or the distal end of the second arm so that the coupled peripheral components have one or more degrees of translation freedom, and preferably three, relative to the cabinet.

According to another embodiment, a dispensing device is provided. The dispensing device may include a cabinet that includes at least one compartment for dispensing health care supplies to a patient and a user interface that is configured to receive input from a user and provide output to the user. The user interface maybe coupled with the cabinet via an articulating arm. The articulating arm may provide the user interface with at least one degree of translational freedom and one degree of rotational freedom relative to the cabinet.

The articulating arm may include a first arm rotationally coupled with the cabinet and a second arm rotationally coupled with the first arm and rotationally coupled with the user interface. In one embodiment, the first arm has a length of between about 5 and about 15 inches and the second arm has a length of between about 10 and about 20 inches. In such a configuration, the articulating arm may have a maximum arc radius of between about 15 inches and about 35 inches. In another embodiment, the first arm has a length of between about 8 and about 12 inches and the second arm has a length of between about 13 and about 17 inches.

The second arm may be rotationally coupled with the user interface so that the user interface is rotatable in a first rotational direction about 300 degrees relative to the second arm. The second arm may also be rotationally coupled with the user interface so that the user interface is rotatable in a second rotational direction about 90 degrees relative to the second arm. The second rotational direction may be orthogonal to the first rotational direction.

According to another embodiment, a method of manufacturing a dispensing device having an adjustable user interface is provided. The method may include providing a cabinet that include at least one compartment for dispensing health care supplies to a patient. The method may also include providing a user interface that is configured to receive input from a user and provide output to the user. The method may further include providing an articulating arm assembly. The user interface may be coupled with the articulating arm assembly and the articulating arm assembly may be coupled with the cabinet so that the articulating arm assembly provides the user interface with at least one and preferably three degrees of translational freedom and one degree of rotational freedom relative to the cabinet.

As described herein, the articulating arm assembly may include a first arm and a second arm. To provide the described motion, a proximal end of the first arm may be rotationally coupled with the cabinet and a proximal end of the second arm may be rotationally coupled with a distal end of the first arm. A distal end of the second arm may be coupled with the user interface. The first arm may be rotationally movable within a first plane and the second arm may be rotationally movable within a second plane. The second plane may be substantially parallel to the first plane. The user interface may be rotationally movable within a third plan and the third plane may be substantially orthogonal to the first and/or second plane.

Coupling the first arm with the cabinet may include coupling the first arm with a side of the cabinet near a top surface and near a back surface of the cabinet. This configuration may minimize the size of the dispensing device while providing a wide range of motion, and thus adjustability, of the user interface. The user interface may be communicatively coupled with a control system of the dispensing device. The control system may be configured to provide one or more operational functions related to dispensing the health care supplies from the dispensing device.

BRIEF DESCRIPTION OF THE DRAWINGS

The present disclosure is described in conjunction with the appended figures.

In the appended figures, similar components and/or features may have the same reference label. Where the reference label is used in the specification, the description is applicable to any one of the similar components having the same reference label.

DETAILED DESCRIPTION OF THE INVENTION

Figure 1:
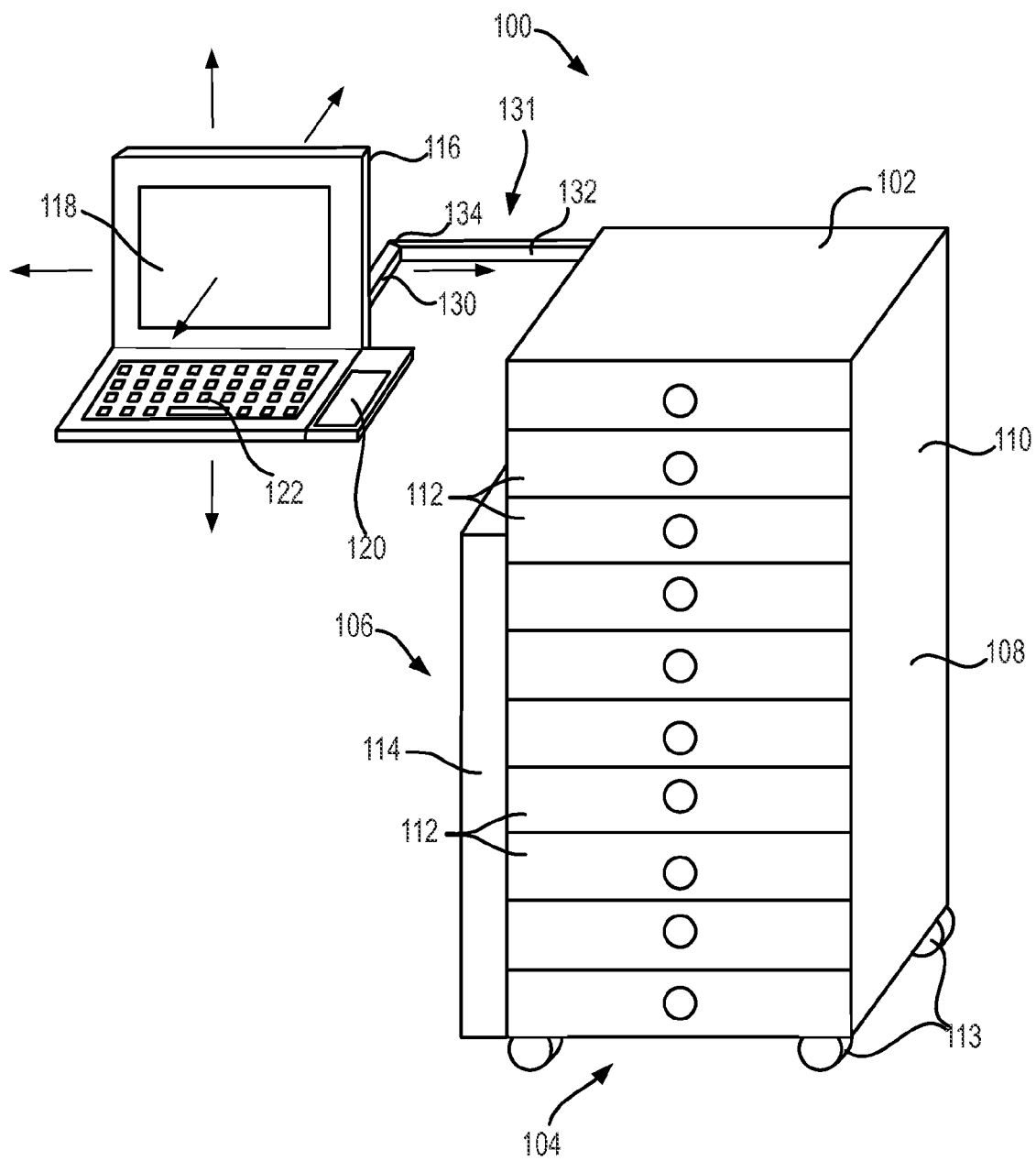
FIG. 1 is a perspective view of an exemplary dispensing unit in accordance with an embodiment of the present invention.

Turning now to FIG. 1, there is shown a medication dispensing unit 100 in accordance with embodiments of the invention. The dispensing unit 100 includes a medication dispensing cabinet 110 having a top surface 102, a bottom surface 104, a left side 106, and a right side 108. Although cabinet 110 may include virtually any cabinet, in one embodiment, cabinet 110 is between about 20 and 30 inches wide, 18 and 26 inches deep, and 40 and 50 inches tall (i.e., measured from the floor to a working top surface). In a specific embodiment, cabinet 110 is approximately 24 inches wide, 22 inches deep, and 43 inches tall. The cabinet 110 includes a plurality of retractable drawers 112. The retractable drawers 112 may hold a plurality of items including patient specific items (e.g., specific medications, syringes, bandages, and the like), generic items or non-patient specific items (e.g., generic bandages, syringes, medications, over the counter medications, and the like), and/or any other item. One or more of the drawers may be secured by locks (not shown) which can be opened only when an authorized user is granted access. The drawers may be divided into bins (not shown) in order to separate supplies and other items stored within the drawers. The specific construction of the drawers 112 can vary depending on the needs of the medical facility in which it is used. One exemplary type of drawer system in a dispensing unit is described in commonly owned U.S. Pat. No. 6,039,467, issued on Mar. 21, 2000 to Holmes, which is hereby incorporated by reference. It should be appreciated that embodiments of the invention are not limited to cabinets of the type shown and, in fact, need not employ drawers. For example, the dispensing unit could alternatively use doors, sliding panels or other features for separating and securing items stored therein. The cabinet 110 also includes wheels 113 to permit the dispensing unit to be wheeled to various locations within the medical facility, such as patient rooms or other locations near a patient or near the location where dispensed items might be needed.

The dispensing unit 100 includes a system controller 114 having a processor and associated memory devices. The system controller 114 may be hidden within cabinet 110 and thus not seen or may be an external device coupled with the dispensing unit 100 as shown in FIG. 1. The dispensing unit 100 also include a user interface 116 linked to the system controller 114 and processor. The user interface 116 includes a keyboard 122, a display device 118 (e.g., LCD with touchscreen), and one or more peripheral devices 120 (see FIGS. 3A-4). The peripheral devices may include a card reader 142, a fingerprint scanner 140, a scanner 144, a mouse (not shown), an RFID device, a printer, touchpad, speakers, proximity sensors, camera, and the like. The dispensing unit 100 may also include a power strip 115 (see FIG. 4A). The keyboard 122 and display 118 of the user interface 116 might be used to enter and select information (for example, enter a user ID/password, select patient information and medications, and so forth).

The user interface 116 and/or peripheral devices 120 may be coupled with dispensing unit 100 by an articulating arm 131 that allows the user interface 116 and/or peripheral devices to move with one or more degrees of freedom with respect to the dispensing unit 100. For example, the articulating arm 131 may provide three degrees of translational freedom (represented by the arrows) and one or more degrees of rotational freedom (rotation around the axes of 1 or more of the arrows) so that a user of the dispensing unit 100 is able to adjust the user interface 116 and/or peripheral devices 120 to a comfortable operating position and/or to free up counter space on tope surface 102. Adjustment may involve vertically adjusting the user interface 116 to change the height of the user interface 116 with respect to the floor, horizontally adjusting the user interface 116 to change the position of the user interface 116 with respect to a side of the cabinet 110 (e.g., the left side 106), and/or adjusting a depth of the user interface 116 to change the position of the user interface 116 with respect to a front face of the cabinet 110. Adjustment may further involve rotationally adjusting the user interface 116 and/or peripheral devices 120 to change a rotational orientation of the user interface 116 with respect to the cabinet 110. The articulating arm 131 may include a first arm segment 132, a second arm segment 130, and one or more pivot points 134 or joints. The articulating arm is described in greater detail in FIGS. 3-5.

The medication dispensing unit 100 may include security measures that control access to the drawers 112 and/or cabinet 110. Access control may be especially useful when the cabinet stores legally controlled substances. In some embodiments, a user of the cabinet (e.g., a nurse or technician) may be required to enter identifying information on keyboard 122 before being allowed access to the drawers 112. The entered information is compared with a list of authorized users, and access is granted only if the entered information is found in the list. The authorization list may reside at system controller 114, or may be on a remote server accessed over a network connection. Alternatively or additionally, a password or other security code may be required, and access may be granted only when the correct code is received.

For example, card reader 142 may be used to authorize a user of the cabinet and provide access to the drawers 112. Each authorized user may carry a card programmed with the user's identifying information. The user can swipe the card through a slot of card reader 142 to provide the identifying information to system controller 114. The identifying information is compared, at system controller 114 or at a remote server, with a list of persons authorized to access cabinet 110, and access is granted only if the information matches or is found on the list. The card carried by the user may be a magnetic stripe card or a smart card, in which case card reader 142 may include a smart card reader.

Similarly, fingerprint reader 140 (or another biometric sensor) may be used by a user to gain access to drawers 112. The user may place a finger on fingerprint reader 140, which reads the person's fingerprint and authenticates the user by checking that the user's fingerprint matches a fingerprint profile of an authorized user. The scanner 144 may also be used to scan an identification badge of a user to authenticate the user and provide access to the drawers 112. The scanner 144 may also scan a patient identification bar code, a bar code of one or medications, and/or scan any other item.

The storage compartments of cabinet 110, such as drawers 112, may be under the control of system controller 114. For example, one or more drawers 112 may include an electronically-controllable locking mechanism, and may only be openable under the control of system controller 114. In addition, system controller 114 may store information about what supplies are stored in which compartments, drawers, and/or bins of cabinet 110. In one usage scenario, a health care worker (e.g., a nurse or technician) may enter, using keyboard 122 or peripheral device 120 (e.g., scanner 144), an identification of a patient who is under the care of the health care worker, and who will need medication during the worker's current rounds. System controller 114 may access the patient's medical file and determine what medications have been prescribed for that patient. System controller 114 may then open only the drawer 112 or drawers containing the prescribed medications for that patient. A particular compartment within the correct drawer 112 and/or the drawer itself may be highlighted, for example with a lighted indicator, to draw the health care worker to the correct medication. The health care worker can then remove the patient's prescribed medication. The level of control exercised by system controller 114 may help in preventing medication and dosing errors, by reducing the likelihood that a health care worker will remove an incorrect medication from medication dispensing cabinet 110. In addition, system controller 114 may document and record which medication was dispensed, and may forward that information to inventory and accounting systems.

Many other features and functions are possible as well. For example, the health care worker may enter his or her identification as well, and system controller 114 may provide access only to those medications and supplies for which the worker is authorized access.

System controller 114 may communicate remotely with other computerized systems, such as medical records systems, inventory and accounting systems, and the like.

The particular arrangement of drawers 112, doors, or other features of a cabinet according to embodiments of the invention may be varied. For example, some cabinets 110 or dispensing units 100 embodying the invention may use only drawers, only doors, or utilize some other access method. Compartments within drawers 112 may also be individually lockable and controllable. Additional types of dispensing units are described in the following commonly owned U.S. patents and patent applications, the contents of which are hereby incorporated by reference: U.S. Pat. No. 6,272,394, issued on Aug. 7, 2001 to Lipps, U.S. Pat. No. 6,385,505, issued on May 7, 2002 to Lipps, U.S. Pat. No. 6,760,643, issued on Jul. 6, 2004 to Lipps, U.S. Pat. No. 5,805,455, issued on Sep. 8, 1998 to Lipps, U.S. Pat. No. 6,609,047, issued on Aug. 19, 2003 to Lipps, U.S. Pat. No. 5,805,456, issued on Sep. 8, 1998 to Higham et al, U.S. Pat. No. 5,745,366, issued on Apr. 28, 1998 to Higham et al., an U.S. Pat. No. 5,905,653, issued on May 18, 1999 to Higham et al., U.S. Pat. No. 5,927,540, issued on Jul. 27, 1999 to Godlewski, U.S. Pat. No. 6,039,467, issued on Mar. 21, 2000 to Holmes, U.S. Pat. No. 6,640,159, issued on Oct. 28, 2003 to Holmes et al., U.S. Pat. No. 6,151,536, issued on Nov. 21, 2000 to Arnold et al., U.S. Pat. No. 5,377,864, issued on Jan. 3, 1995 to Blechl et al., U.S. Pat. No. 5,190,185, issued on Mar. 2, 1993 to Blechl, U.S. Pat. No. 6,975,922, issued on Dec. 13, 2005 to Duncan et al., U.S. Pat. No. 7,571,024, issued on Aug. 4, 2009 to Duncan et al., U.S. Pat. No. 7,835,819, issued on Nov. 16, 2010 to Duncan et al., U.S. Pat. No. 6,011,999, issued on Jan. 4, 2000 to Holmes, U.S. Pat. No. 7,348,884, issued on Mar. 25, 2008 to Higham, U.S. Pat. No. 7,675,421, issued on Mar. 9, 2010 to Higham, U.S. Pat. No. 6,170,929, issued on Jan. 9, 2001 to Wilson et al., U.S. Patent Application Publication No. 2008/0319579 of Vahlberg et al., published on Dec. 25, 2008, and U.S. Patent Application Publication No. 2010/0042437 of Levy et al., published on Feb. 18, 2010.

Figure 2:
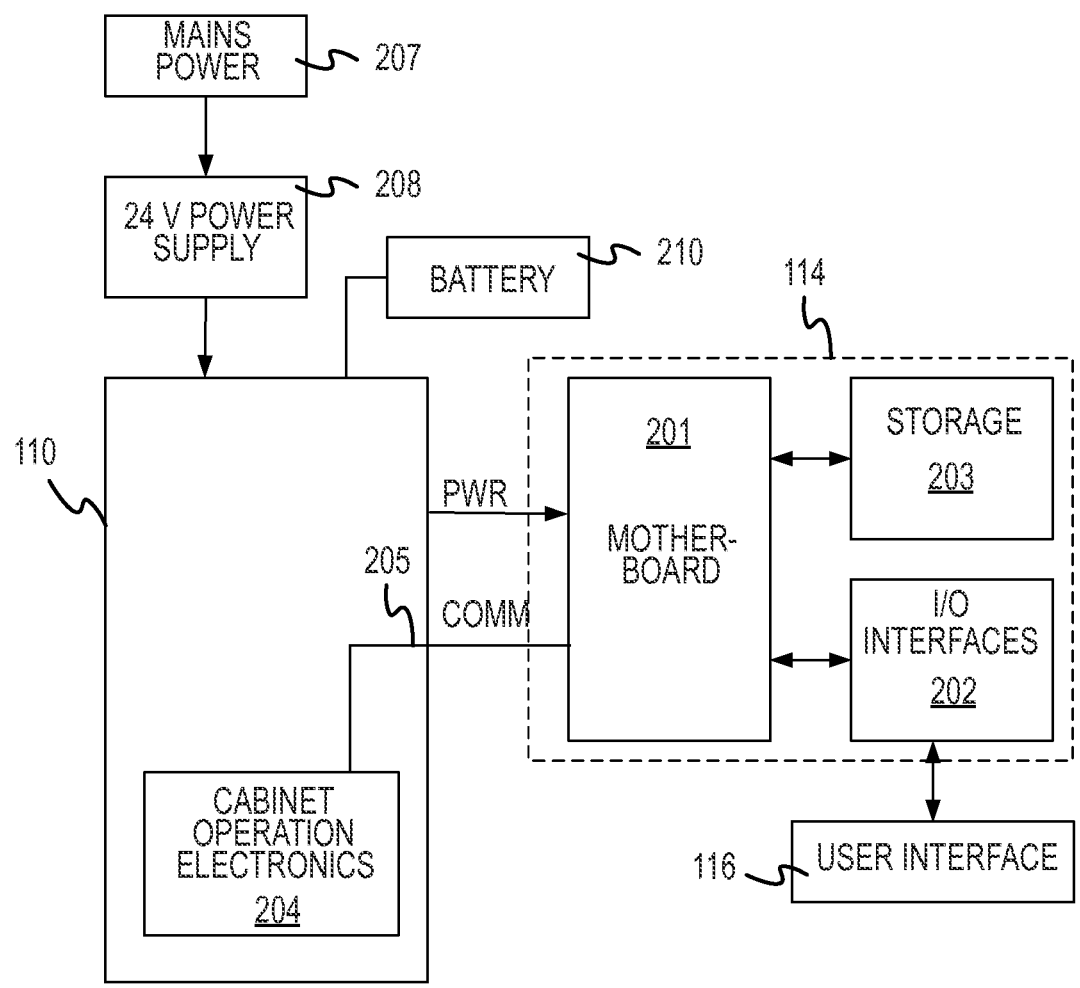
FIG. 2 illustrates an example electronic architecture of a dispensing unit and control system in accordance with an embodiment of the present invention.

FIG. 2 illustrates an embodiment of electronic architecture of dispensing unit 100 and system controller 114. As explained above and illustrated in FIG. 2, system controller 114 may include a processor, input/output interfaces, storage, and other components. In FIG. 2, system controller 114 includes a motherboard 201 that may include a microprocessor, expansion card slots, volatile memory, nonvolatile memory, and other computer system components. The volatile memory may include random access memory (RAM) for use as temporary program and data storage. The nonvolatile memory may include any combination of read only memory (ROM), flash memory, and other kinds of nonvolatile memory, and may hold such items as boot code for motherboard 201, system settings, a basic input/output system (BIOS) and other items. In some embodiments, at least some of the contents of the nonvolatile memory may be remotely reprogrammable.

System controller 114 also includes input/output (I/O) interfaces 202, which may interface with user interface 116 (e.g., display 118, keyboard 122, scanner 144, fingerprint scanner 140, card reader 142, and the like). System controller 114 further comprises storage 203, which may be, for example, long-term storage such as one or more hard disk or solid state drives. Storage 203 may store an operating system for motherboard 201, may store data such as an inventory of the cabinet, and may hold program instructions for control of the operation of the cabinet.

Cabinet 110 may include cabinet electronics 204 such as various actuators, indicators, and other components involved in controlling the cabinet, for example to lock and unlock drawers or doors under control of system controller 114. Cabinet electronics 204 may optionally also include one or more additional microprocessors or other logic circuitry. Motherboard 201 communicates with cabinet electronics 204 through communications link 205.

Both system controller 114 and cabinet electronics 204 require electrical power for operation. Cabinet 110 is electrically coupled with one or more power sources, such as mains power 207 and battery 210. The cabinet 110 may include a power distribution and communications circuit board (not shown) that conditions and distributes power to system components. A first power supply 208 may rectify the voltage obtained from mains 207 and supply a single DC voltage to cabinet 110.

Figure 3A:
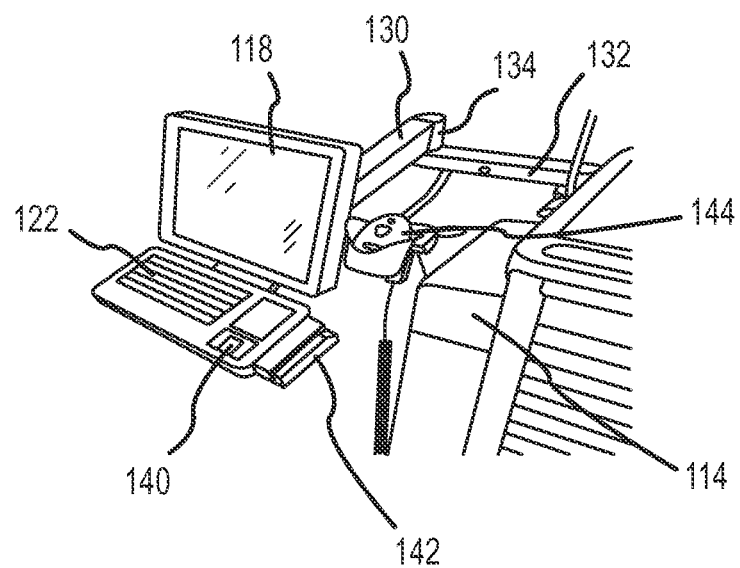
FIGS. 3A-C illustrate various views of the dispensing unit of FIG. 1 and an articulating arm of the dispensing unit in accordance with an embodiment of the invention.
Figure 4A:
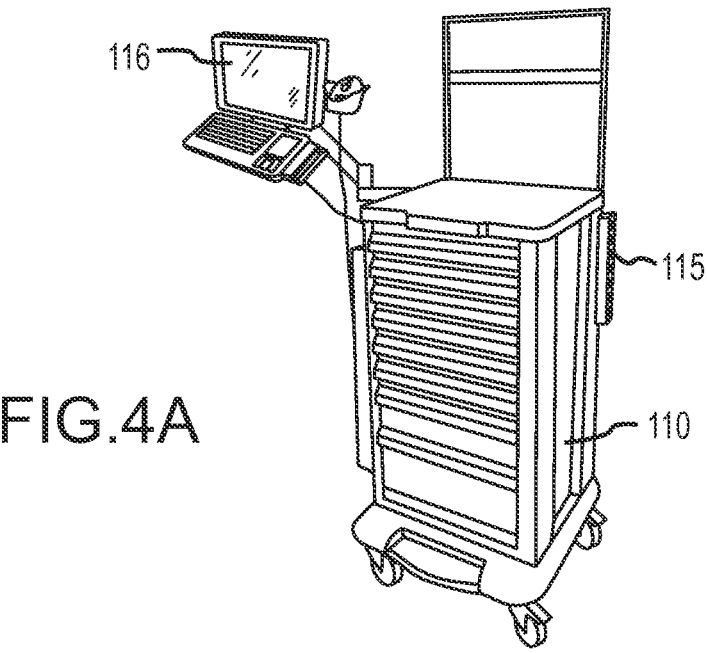
FIGS. 4A-E illustrate perspective views of the dispensing unit of FIG. 1 being adjusted and used in accordance with an embodiment of the present invention.
Figure 4B:
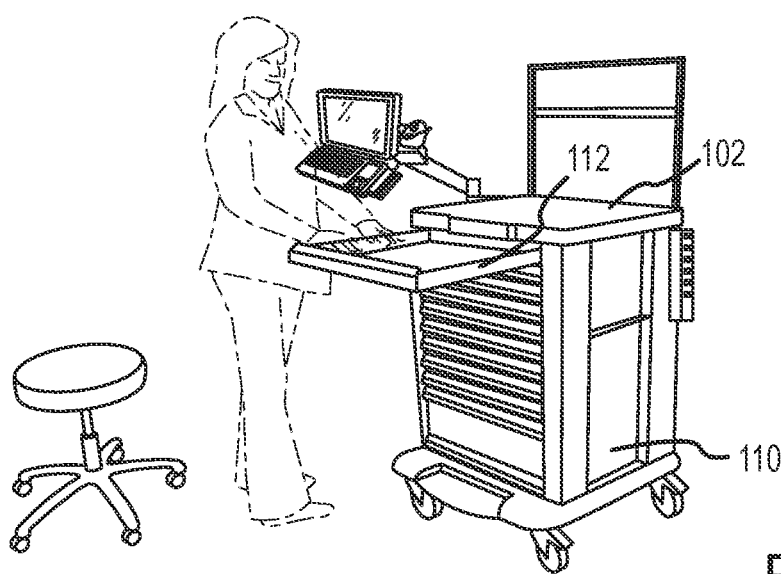
Figure 4C:
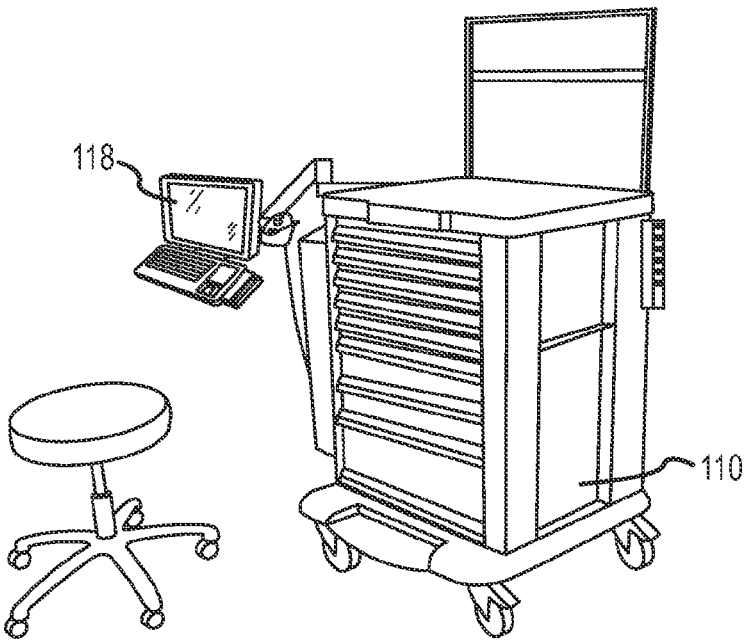
Figure 4D:
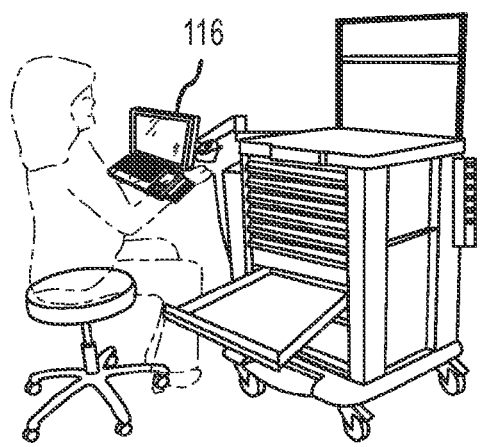
Figure 4E:
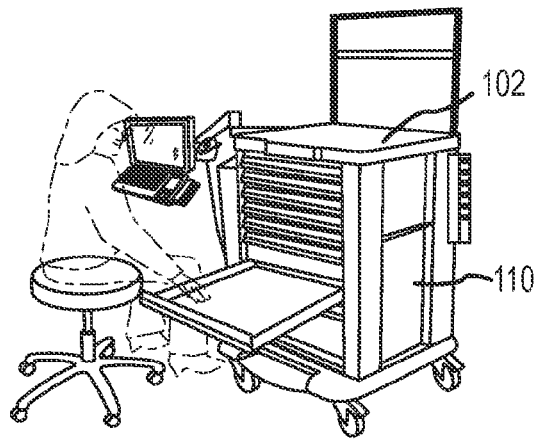
Figure 5:
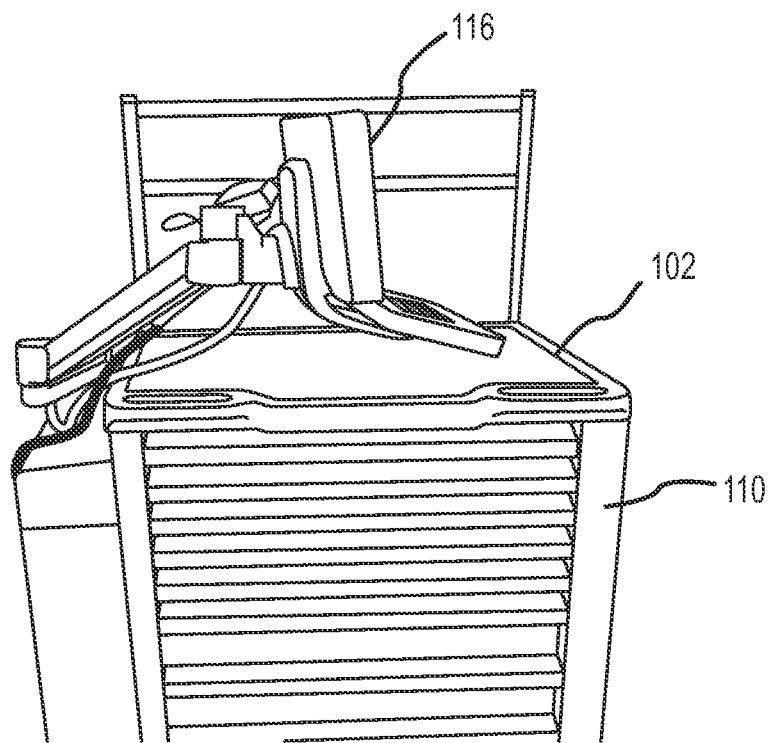
FIG. 5 illustrates the dispensing unit of FIG. 1 having a user interface adjusted and positioned over a top surface of a cabinet in accordance with an embodiment of the present invention.

FIGS. 3-5 illustrate the medication dispensing device or unit 100 of FIG. 1 and further illustrates various aspects of user interface 116 and articulating arm 131. FIG. 3A shows user interface 116 including a display device 118, a keyboard 122, a fingerprint scanner 140, a card reader 142, a scanner 144 (e.g., bar code scanner), and the like. These devices may function as is commonly known in the art and/or as described herein. In one embodiment, keyboard 122 may be rotationally coupled with second arm segment 130 and/or display device 118 so that keyboard 122 may be rotationally adjusted vertically relative to display device 118 to accommodate various user needs and/or preferences. For example, keyboard 122 may be adjustable so that an angle between keyboard 122 and display device 118 is variable between less than 90 degrees to 180 degrees or more. The user interface 116 and peripheral devices are communicatively coupled with system control 114.

FIG. 3A further illustrates user interface 116 coupled with cabinet 110 by first arm segment 132 and second arm segment 130. First arm segment 132 is rotationally coupled with second arm segment 130 by second pivot point or joint 134.

Figure 3B:
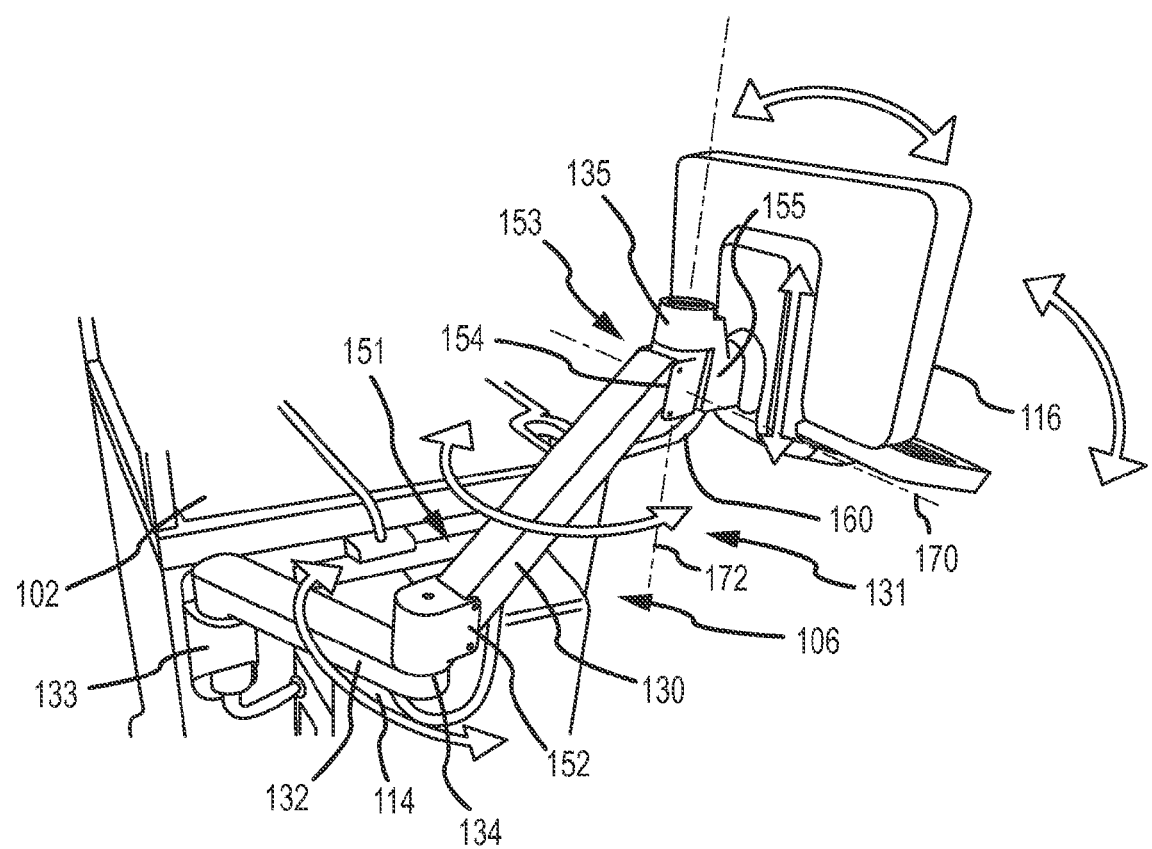
Figure 3C:
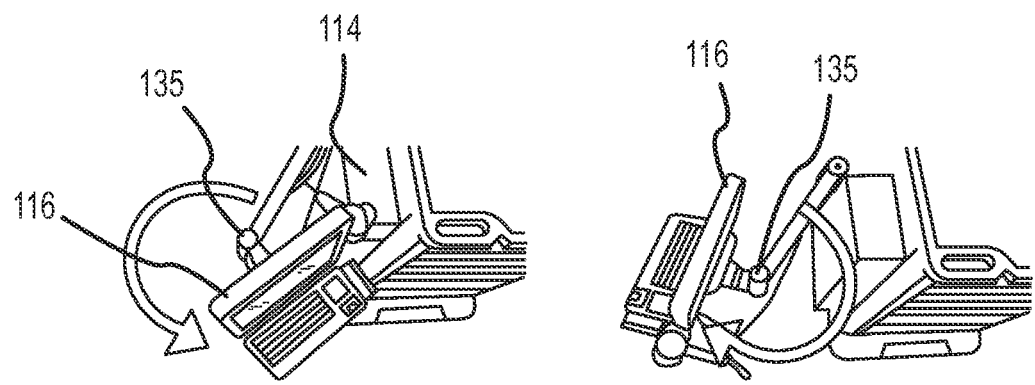

FIG. 3B provides a side perspective view of dispensing unit 100 and provides additional detail of articulating arm 131. Articulating arm 131 includes first arm segment 132 and second arm segment 130. First arm segment 132 is rotationally coupled to a side of cabinet 110 at first pivot joint 133. First arm segment 132 is preferably connected to the side of cabinet 110 near the back and top surfaces of cabinet 110. For example, in one embodiment, first pivot joint 133 is between about 2 and about 10 inches from the back surface of cabinet 110 and between about 2 and about 10 inches from the top surface of cabinet 110. In another embodiment, first pivot joint 133 is between about 2 and about 6 inches from the back and/or top surface of cabinet 110. Coupling first arm segment 132 to the cabinet 110 in this manner (i.e., to the side of the cabinet near the top and back surfaces) allows the first arm segment 132 to be located out of the way of other components of cabinet 110, and/or minimized space requirements of the cabinet, while providing a broad range of motion for user interface 116. In alternative embodiments, first arm segment 132 may be coupled with the top surface or the back surface of cabinet 110.

First pivot joint 133 allows first arm segment 132 to rotationally move relative to cabinet 110 about an axis substantially parallel to a side of the cabinet 110 (e.g., left side 106). The fore and aft movement of first arm segment 132 is shown by the arrow drawn directly above first arm segment 132. In one embodiment, first pivot joint 133 provides first arm segment 132 with a 180 degree range of motion relative to cabinet 110. This range of motion allows display device 118 to be positioned either behind or in front of cabinet 110 or anywhere on the side of the cabinet. In another embodiment, the range of motion may be greater than 180 degrees. For example, if first pivot joint 133 is located at corner of cabinet 110, the range of motion may be 270 degrees and may only be restricted by the cabinet 110. Similarly, if the first pivot joint 133 is located on or above top surface 102, the range of motion may be 360 degrees.

First arm segment 132 is rotationally coupled with second arm segment 130 by a second pivot joint 134. Second pivot joint 134 allows second arm segment 130 to pivot in relation to first arm segment 132 about an axis that is substantially parallel to the pivot axis of first pivot joint 133. The rotational motion of second arm segment 130 with respect to first arm segment 132 is illustrated by the arrow directly above second arm segment 130. Second pivot joint 134 may provide second arm segment 130 with a range of motion up to 360 degrees so that second arm segment 130 is able to pivot or rotate entirely around first arm segment 132. This motion allows display device 118 to be positioned virtually anywhere to accommodate various user needs and/or preferences. For example, a user may rotate display device 118 above top surface 102 of cabinet 110 to minimize space, to position display device 118 above items positioned on top surface 102 so as to conveniently work with keyboard 122 and the items on top surface 102, and/or for various other reasons. The user may then reposition display device 118 in front of cabinet 110 or on the side of cabinet 110 when additional workspace on top surface 102 is desired and/or the user is working with other components or items positioned in front of or on the side of cabinet 110, such as when the user is stocking or removing items from the cabinet 110's drawers. The user may additionally vertically raise display device 118 to a level of each drawer to conveniently stock or withdrawn supplies from that drawer.

Second arm segment 130 includes a first vertical coupling 152 at a first end 151 of second arm segment 130 and a second vertical coupling 154 at a second end 153. First and second vertical couplings, 152 and 154, allow the second end 153 to be vertically adjusted with respect to first end 151 as shown by the vertical arrow and further illustrated in FIGS. 3A, 3B, and 4A-4D. Coupled with second end 153 is user interface 116 and/or one or more peripheral devices (not shown). According to several embodiments, first and second vertical pivot joints, 152 and 154, provide user interface 116 with a vertical range of motion between 0 and 30 inches, 10 and 30 inches, 15 and 25 inches, 15 and 20 inches, and the like, although it should be realized that other ranges of motion are possible. In a specific embodiment, second arm segment 130 provides about 16 inches of vertical adjustment, which allows user interface 116 to be adjusted anywhere in between a height of about between 31 inches above the floor (measured from the floor to keyboard 122) corresponding to a sitting position to about 47 inches above the floor corresponding to a standing position.

In one embodiment, second vertical coupling 154 allows user interface 116 to be rotationally adjusted about axis 170 (illustrated by the arrow in front of user interface 116) so that user interface 116 may be tilted toward or away from the user to accommodate users of various height and/or to accommodate other user needs and/or preferences. In another embodiment, second coupling 154 is configured so that user interface 116 maintains a tilt orientation (e.g., approximately vertical) as user interface 116 is vertically adjusted.

A third pivot joint 135 couples user interface 116 and/or peripheral devices with second arm segment 130. A third arm 155 may extend from user interface 116 to third pivot joint 135. Third pivot joint 135 allows rotational movement of user interface 116 and/or the peripheral devices about axis 172 so that user interface 116 is rotatable relative to second arm 130. The rotational movement of user interface 116 about axis 172 of third pivot joint 135 is shown by the arrow directly above user interface 116 and further illustrated by FIG. 3C. In one embodiment, third pivot joint 135 provides user interface 116 and/or peripheral devices with up to 300 degrees of rotational movement about the axis of third pivot joint 135. Although 300 degrees of rotational movement is typically sufficient for most needs of user interface 116, the rotational movement of user interface 116 may be increased by increasing the separation between user interface 116 and second arm segment 130. Alternatively, the position of user interface 116 with respect to arm segment 130 may be such that contact 130 between these components is minimized or eliminated and more rotational movement is possible. For example, user interface 116 may be placed above or below the arm segment 130 and thereby allow up to full 360 degree rotation. Third pivot joint 135 allows user interface 116, and thus display device 118, to be rotated to provide multiple viewing angles.

Figure 7:
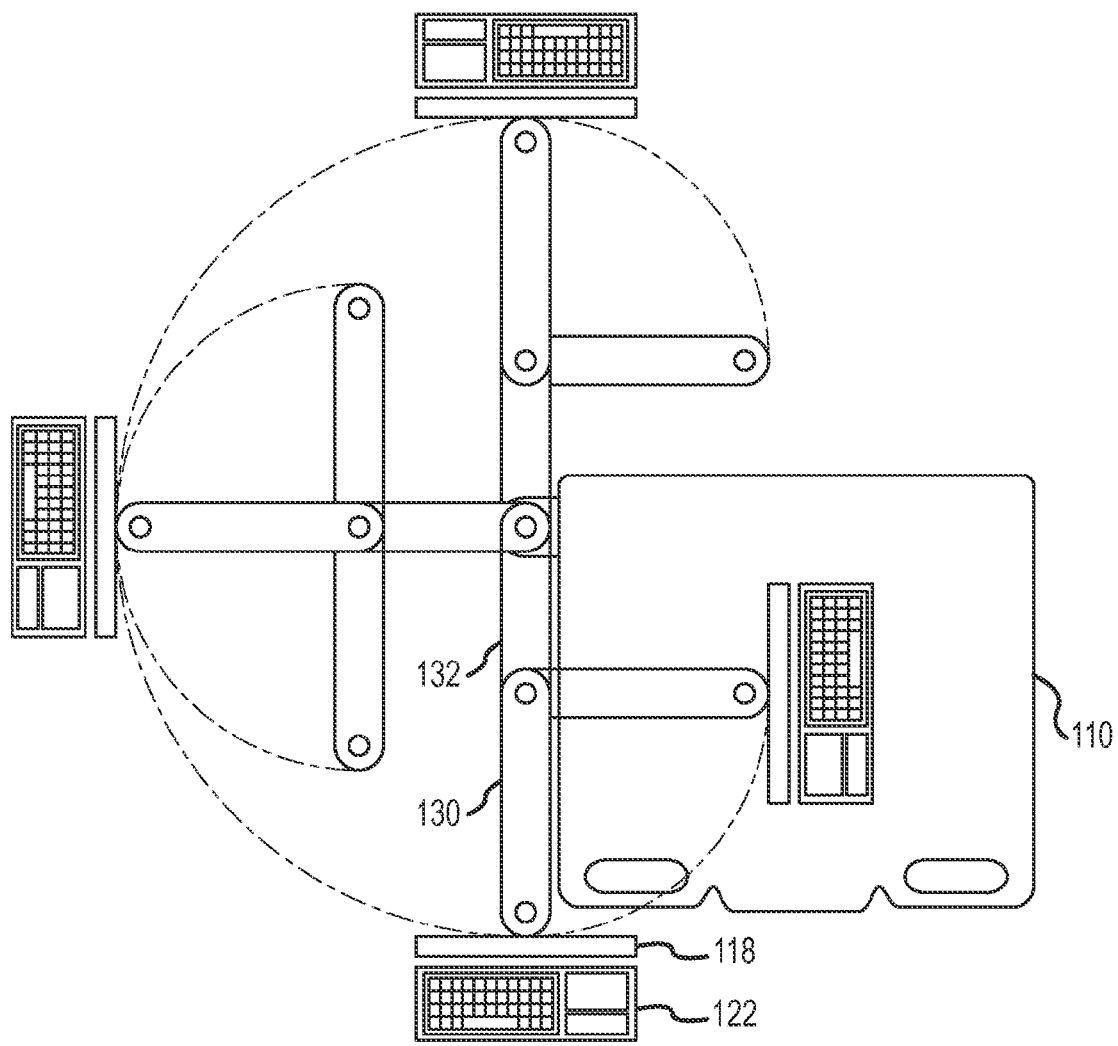
FIG. 7 illustrates a top view of a barrel shaped range of motion that may be provided by the articulating arm assemblies described herein.

In one embodiment, first arm segment 132 has a length of between about 5 and about 15 inches, and more commonly between about 8 and about 12 inches. This length may be measured from the axis of the first joint 133 to second joint 134. Second arm segment 130 may have a length of between about 10 and about 20 inches, and more commonly between about 13 and 17 inches. This length may be measured from the axis of the second joint 134 to third joint 135. In such embodiments, the first and second arm segments, 132 and 130, provide an arc radius of between about 15 inches and about 35 inches, and more commonly about 22 to about 30 inches. In one embodiment, the user interface 116 extends beyond the second arm segment 130 up to about 12 inches, which extends the arc radius up to about 47 inches. As described above, second arm segment 130 may be vertically adjustable between about 0 and 30 inches, and more commonly between about 10 and 20. The described articulating arm assembly may provide user interface 116 with a barrel shaped range of motion relative to cabinet 110 as shown in FIG. 7. As shown in the figure, the barrel shaped range of motion may be interrupted on one side by cabinet 110, such as when first arm segment 132 contacts cabinet 110. The barrel shaped range of motion may have a maximum diameter of about 60 inches (i.e., a maximum radius of about 30 inches), and more commonly about 50 inches. User interface 116 may be movable virtually anywhere within the barrel shaped range of motion. The vertical component of the barrel shaped range of motion may be up to about 30 inches, and more commonly between about 13 and 17 inches. As can be appreciated, the diameter and radius of the barrel decrease as the user interface is vertically adjusted from a center position.

First, second, and/or third pivot joints, 133, 134, and 135, may be any type of pivot joint including bushings, bearings, and the like. One or more electrical lines or cables 160 may extend along first arm segment 132 and second arm segment 130 to electrically couple user interface 116 and/or the other peripheral devices with system controller 114 and/or to couple user interface 116 with battery 210 and/or power supply 208. Although not necessarily shown, articulating arm 131 may include other pivot joints, such as a pivot joint that allows user interface 116 to be rotated clockwise and counterclockwise.

Articulating arm 131 allows user interface 116 and/or the peripheral devices to be positioned in multiple locations to fit the users need. For example, first and second arm segments, 132 and 130; first, second, and third pivot joints, 133, 134, and 135; and first and second vertical pivot joints, 142 and 144, allow the user interface 116 and/or peripheral devices to be positioned virtually anywhere on a side (left or right side, 106 and 108), in front, or behind cabinet 110. Articulating arm 131 may be conveniently coupled to the side of cabinet 110 to minimize interference with other components of cabinet 110 and/or minimize the overall size of the unit, to provide a completely empty and clear work surface (e.g., top surface 102), and the like.

For example, user interface 116 and/or the peripheral devices may be positioned in a vertically raised position with respect to cabinet 110 as illustrated in FIG. 4A. In such a position, a user is able to use cabinet 110 and user interface 116 while standing as illustrated in FIG. 4B. This configuration allows the user to easily transport cabinet 110 from one area to another, such as between patient rooms, and to operate user interface 116 without sitting down or having to move the cabinet 110 or walk around cabinet 110.

The user may grasp and position user interface 116 in a comfortable position, such as at an eye or chest level and/or tilt user interface 116 and/or keyboard 122 to a desired relative position. The adjustability of the user interface 116 allows the user to position user interface 116 and/or other peripheral devices on a side of cabinet 110 to free up space on top surface 102, which provides additional work space.

As described herein, system control 114 may authenticate a user via user interface 116 and/or one or more of the peripheral devices and unlock one or more drawers 112, bins, cabinets, and the like. The user may take one or more supplies, medications, and the like from drawer(s) 112 and use top surface 102 in administering treatment to a patient.

Similarly, user interface 116 and/or peripheral devices may be positioned in a vertically lowered position with respect to cabinet 110 as illustrated in FIG. 4C. In such a position, a user is able to use cabinet 110 and user interface 116 while sitting on a chair or stool as illustrated in FIGS. 4D & E. This allows user interface 116 and/or the peripheral devices to be adjusted to accommodate a user's sitting position, such as when the user is accessing lower drawers 112 of cabinet 110 and/or using cabinet 110 in a stationary position for a prolonged amount of time (e.g., when a user is refilling cabinet drawers with supplies and medication). User interface 116 may be positioned in front of the device when the user is accessing and/or scanning items at a far end of the cabinet or drawer. FIG. 4D illustrates a user swiping an identification card through a card reader. As shown in FIG. 4E, the user may be authenticated and/or authorized and access may be granted to a drawer 112, bin, or cabinet specific to an identified patient. The user may then administer treatment and/or medication to the patient.

FIG. 5 illustrates user interface 116 being positioned over top surface 102 of cabinet 110. Such a configuration may be employed when the dispensing unit 100 is being stored, is inoperative, being refilled, being transported between rooms or other areas such as to protect user interface 116, being shipped to a care facility or other location, or may be used when a compact configuration is otherwise needed and/or desired. Such a configuration reduces the overall footprint of dispensing unit 100. In addition, in such a configuration, the display device of user interface 116 may be pivoted about third pivot joint 135 so that the display device faces a user accessing drawers 112.

User interface 116 and/or peripheral devices may further be adjusted depending on the need of a patient, such as when a patient's bar code is being read and/or the patient is being shown information on display device 118.

Articulating arm 131 allows the user to grab user interface 116 and reposition it without having to activate any buttons or levers—e.g., the user is able to adjust user interface 116 to a new position and simply let go. Articulating arm 131 holds user interface 116 in the adjusted position. Articulating arm has provisions to allow cabling for user interface 116 and/or the peripheral devices to be captured and move with the articulating arm. Articulating arm 131 is easily adjusted to allow different amounts of counter balance to the weight of user interface 116. The counter balance can be adjusted to accommodate increased weights, such as when additional peripheral devices are attached to user interface 116 and/or other objects are supported by articulating arm 131. The user interface 116 and peripheral devices (e.g., scanner 144, fingerprint scanner 140, and the like) may stay together and move as a group coupled at the end of articulating arm 131.

Figure 6:
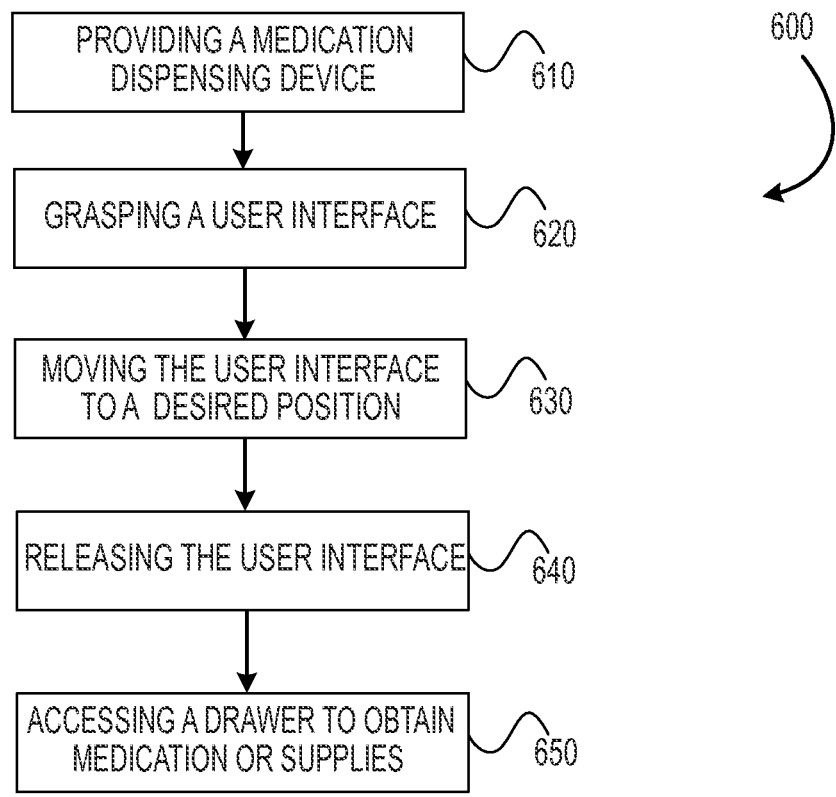
FIG. 6 illustrates a method of using a medication dispensing unit having an adjustable user interface in accordance with an embodiment of the present invention.

FIG. 6 illustrates a method of using a medication dispensing device having an adjustable user interface as described herein. At block 610, a medication dispensing device is provided. The dispensing device may have a user interface, a control system, a cabinet, an articulating arm, and the like as described herein. At block 620, the user interface is grasped, such as by a user grasping a display device of the user interface by hand. At block 630, the user interface is moved to a desired position or location with respect to the cabinet, such as by the user moving the display device of the user interface. The articulating arm, which provides multiple degrees of translation and/or rotational freedom, allows the user interface to be adjusted and moved with respect to the cabinet. At block 640, the user interface is released, such as by the user letting go of the display device. At block 650, a drawer of the cabinet may be accessed to obtain supplies and/or medication that is to be administered to a patient to treat the patient.

Figure 8:
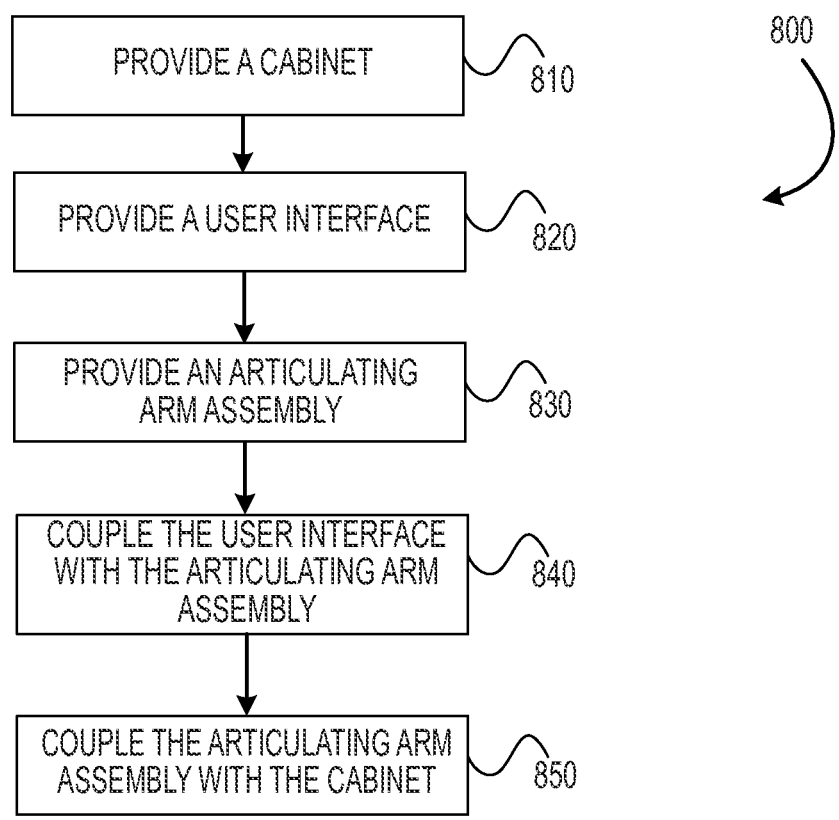
FIG. 8 illustrates a method of manufacturing a dispensing device having an adjustable user interface according to an embodiment of the present invention.

FIG. 8 illustrates a method 800 of manufacturing a dispensing device having an adjustable user interface. At block 810, a cabinet including at least one compartment for dispensing health care supplies to a patient is provided. At block 820 a user interface configured to receive input from a user and provide output to the user is provided. At block 830, an articulating arm assembly is provided. As described herein, the articulating arm assembly may include a first arm and a second arm. At block 840, the user interface may be coupled with the articulating arm assembly and at block 850, the articulating arm assembly may be coupled with the cabinet. As described herein, the articulating arm assembly may provide the user interface with at least three degrees of translational freedom and one degree of rotational freedom relative to the cabinet.

In one embodiment, the articulating arm assembly coupling process may involve rotationally coupling a proximal end of the first arm with the cabinet, rotationally coupling a proximal end of the second arm with a distal end of the first arm; and rotationally coupling a distal end of the second arm with the user interface. The first arm may be coupled with a side of the cabinet near a top surface and near a back surface of the cabinet. The coupling of the arms may be such that the first arm is rotationally movable within a first plane, the second arm is rotationally movable within a second plane that is substantially parallel with the first plane, and the user interface is rotationally movable within a third plan that is substantially orthogonal to the first plane and/or second plane.

The method may further include communicatively coupling the user interface with a control system of the dispensing device. The control system may be configured to provide one or more operational functions related to dispensing the health care supplies from the dispensing device.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A dispensing device including an adjustable user interface, the dispensing device comprising:
   a cabinet including at least one compartment for dispensing health care supplies to one or more patients;
   a control system including a processor and memory device, the control system being configured to provide one or more operational functions related to dispensing the health care supplies;

a user interface communicatively coupled with the control system, the user interface being configured to receive input from a user and provide output to the user;

a plurality of peripheral devices including a bar code scanner, a card reader, a keyboard, and a speaker; and an articulating arm assembly coupled with the user interface, the plurality of peripheral devices, and the cabinet, the articulating arm assembly providing the user interface and the plurality of peripheral devices with at least three degrees of translational freedom and one degree of rotational freedom relative to the cabinet, the articulating arm assembly comprising:

a first arm having a proximal end coupled directly to a side of the cabinet via a first joint that is positioned within 2 to 10 inches of a top surface of the cabinet and within 2 to 10 inches of a back surface of the cabinet so that the arm extends from a upper rear corner of the cabinet, the first joint enabling up to about 180 degrees of rotational movement of the first arm within a horizontal plane about the side of the cabinet;

a second arm having a proximal end coupled directly to a distal end of the first arm via a second joint that extends vertically upward from the distal end of the first arm, the second joint enabling 360 degrees of rotational movement of the second arm in the horizontal plane relative to the first arm and cabinet and enabling rotational movement of the second arm in a vertical plane so that the user interface has a vertical range of motion of up to 30 inches; and a counter balance that is adjustable to accommodate an increase in weight when additional peripheral devices are attached to the user interface or other objects are supported by the articulating arm;

wherein the user interface and the plurality of peripheral devices are coupled to a distal end of the second arm via a third joint to enable the user interface and the plurality of peripheral device to stay together and be translationally and rotationally moved as a group at the end of the articulating arm, the third joint enabling up to about 300 degrees of rotational movement of the user interface and the plurality of peripheral devices are in the horizontal plane and the third joint also enabling up to about 90 degrees of rotational movement of the user interface in the vertical plan and clockwise and counterclockwise rotation of the user interface about an axis orthogonal to a face of the user interface.

2. The dispensing device of claim 1, wherein the first arm is coupled with a side of the cabinet such that the articulating arm assembly provides the user interface with a barrel shaped range of motion relative to the cabinet, the barrel shaped range of motion being interrupted on one side by the cabinet and having a maximum barrel diameter of about 60 inches, wherein the user interface is movable within the barrel shaped range of motion.

3. The dispensing device of claim 1, wherein the user interface comprises a display device, the keyboard being rotationally adjustable relative to the display device.

4. The dispensing device of claim 3, wherein the control system is configured to authenticate a user and perform one or more functions selected from the group consisting of:
unlocking a drawer;
identifying medication or supplies for a patient;
tracking usage of a medication or supply; and
communicating information with a system of a health care facility.

5. A dispensing device comprising:
a cabinet including at least one compartment for dispensing health care supplies to a patient;
a user interface configured to receive input from a user and provide output to the user, the user interface including a display and a keyboard;
a plurality of peripheral devices coupled with the user interface, the plurality of peripheral devices including a bar code scanner and a card reader; and
an articulating arm that couples the user interface and the plurality of peripheral devices with the cabinet, the articulating arm being coupled with a side of the cabinet near a back surface and a top surface thereof, the articulating arm extending laterally from the side of the cabinet and having three degrees of translational freedom and one degree of rotational freedom relative to the cabinet to enable the user interface and the plurality of peripheral device to stay together and be translationally and rotationally moved as a group at the end of the articulating arm and relative to the cabinet, the articulating arm including:
a first arm rotationally coupled with the cabinet; and
a second arm rotationally coupled with the first arm and rotationally coupled with the user interface and the plurality of peripheral devices such that the user interface and the plurality of peripheral devices are: 1) rotatable horizontally about 300 degrees relative to the second arm, 2) rotatable vertically about 90 degrees relative to the second arm, 3) rotatable clockwise and counterclockwise about an axis that is orthogonal to a face of the user interface.

6. The dispensing device of claim 5, wherein the first arm comprises a length of between about 5 and about 15 inches, and wherein the second arm comprises a length of between about 10 and about 20 inches such that the articulating arm has a maximum arc radius of between about 15 inches and about 35 inches.

7. The dispensing device of claim 6, wherein the first arm comprises a length of between about 8 and about 12 inches and the second arm comprises a length of between about 13 and about 17 inches.

8. A method of manufacturing a dispensing device having an adjustable user interface, the method comprising:
providing a cabinet including at least one compartment for dispensing health care supplies to a patient;
providing a user interface configured to receive input from a user and provide output to the user;
providing a plurality of peripheral devices including a bar code scanner, a keyboard, and a card reader; and
providing an articulating arm assembly, the articulating arm assembly including:
a first arm having a proximal end and a distal end;
a second arm having a proximal end and a distal end, the proximal end of the second arm being directly coupled to the distal end of the first arm; and
a counter balance that is adjustable to accommodate additional peripheral devices or other objects that are supported by the articulating arm;
coupling the user interface and the plurality of peripheral devices with the distal end of the second arm so that the plurality of peripheral device stay together and are translationally and rotationally movable as a group relative to the cabinet at the end of the articulating arm and so that the user user interface is rotatable at the end of the articulating arm up to about 300 degrees of in the horizontal plane, up to about 90 degrees in the vertical plan, and clockwise and counterclockwise about an axis orthogonal to a face of the user interface; and coupling the proximal end of the first arm to a side of the cabinet, the articulating arm assembly providing the user interface and the plurality of peripheral devices with at least three degrees of translational freedom and one degree of rotational freedom relative to the cabinet.

9. The method of claim 8, wherein the method further comprises:

rotationally coupling the proximal end of the first arm with the cabinet;

rotationally coupling the proximal end of the second arm with the distal end of the first arm; and rotationally coupling the distal end of the second arm with the user interface and the plurality of peripheral devices.

10. The method of claim 9, wherein:

the first arm is rotationally movable within a first plane;

the second arm is rotationally movable within a second plane substantially parallel to the first plane; and the user interface is rotationally movable within a third plan substantially orthogonal to the first plane.

11. The method of claim 9, wherein coupling the first arm with the cabinet comprises coupling the first arm with a side of the cabinet near a top surface and near a back surface of the cabinet.

12. The method of claim 8, further comprising communicatively coupling the user interface with a control system of the dispensing device, the control system being configured to provide one or more operational functions related to dispensing the health care supplies from the dispensing device.

13. A dispensing device including an adjustable user interface, the dispensing device comprising:

a cabinet including at least one compartment for dispensing health care supplies to one or more patients;

a control system including a processor and memory device, the control system being configured to provide one or more operational functions related to dispensing the health care supplies;

a user interface communicatively coupled with the control system, the user interface being configured to receive input from a user and provide output to the user; and an articulating arm assembly coupled with the user interface and the cabinet, the articulating arm assembly providing the user interface with at least three degrees of translational freedom and one degree of rotational freedom relative to the cabinet, the articulating arm assembly comprising:

a first arm having a proximal end coupled directly to a side of the cabinet via a first joint that is positioned within 2 to 10 inches of a top surface of the cabinet and within 2 to 10 inches of a back surface of the cabinet so that the arm extends from a upper rear corner of the cabinet, the first joint enabling up to about 180 degrees of rotational movement of the first arm within a horizontal plane about the side of the cabinet; and a second arm having a proximal end coupled directly to a distal end of the first arm via a second joint that extends vertically upward from the distal end of the first arm, the second joint enabling 360 degrees of rotational movement of the second arm in the horizontal plane relative to the first arm and cabinet and enabling rotational movement of the second arm in a vertical plane so that the user interface has a vertical range of motion of up to 30 inches;

wherein the user interface is coupled to a distal end of the second arm via a third joint, the third joint enabling up to about 300 degrees of rotational movement of the user interface in the horizontal plane, enabling up to about 90 degrees of rotational movement of the user interface in the vertical plan, and clockwise and counterclockwise rotation of the user interface about an axis orthogonal to a face of the user interface.

\* \* \* \* \*